United States Patent [19]
Sleytr et al.

[11] Patent Number: 4,886,604

[45] Date of Patent: * Dec. 12, 1989

[54] STRUCTURE WITH MEMBRANES HAVING CONTINUOUS PORES

[76] Inventors: Uwe Sleytr, 10, Parhamerplatz, A-1170 Vienna; Margit Sara, 90/2/24 Vorgartenstr., A-1200 Vienna, both of Australia

[*] Notice: The portion of the term of this patent subsequent to Jun. 21, 2005 has been disclaimed.

[21] Appl. No.: 916,517

[22] PCT Filed: Dec. 23, 1985

[86] PCT No.: PCT/AT85/00060

§ 371 Date: Aug. 19, 1986

§ 102(e) Date: Aug. 19, 1986

[87] PCT Pub. No.: WO86/03685

PCT Pub. Date: Jul. 3, 1986

[30] Foreign Application Priority Data

| Dec. 21, 1984 | [AU] | Australia | 406984 |
| Mar. 6, 1985 | [ZA] | South Africa | 851706 |
| Nov. 8, 1985 | [AU] | Australia | 324785 |

[51] Int. Cl.$^4$ ............................................. B01D 13/00
[52] U.S. Cl. .................................. 210/653; 210/490; 427/245
[58] Field of Search ............ 210/500.37, 440, 653, 210/639, 650, 321.1, 500.27, 500.21, 652; 427/245, 246, 247

[56] References Cited

U.S. PATENT DOCUMENTS

| 3,593,855 | 7/1971 | Staha | 210/500.27 |
| 3,736,204 | 5/1973 | Meriwemer | 210/490 X |
| 3,892,665 | 7/1975 | Steigelmann et al. | 210/490 |
| 4,008,126 | 2/1977 | Keyes | 435/180 X |
| 4,012,324 | 3/1977 | Gregor | 210/500.37 |
| 4,239,714 | 12/1980 | Sparks | 210/500.21 X |
| 4,634,530 | 1/1987 | Kuder et al. | 210/500.27 X |
| 4,661,526 | 4/1987 | Ford | 210/500.38 X |

*Primary Examiner*—Frank Spear
*Attorney, Agent, or Firm*—Bierman and Muserlian

[57] ABSTRACT

A method for producing a structure comprising at least one membrane with continuous pores having a diameter range of 1 to 8 nm extending along plane, curved, cylindrical or vesicular surfaces consisting essentially of at least one layer of contiguous identical protein containing molecules which molecules are arranged to form a crystal lattice defining continous pores free of said molecules, the membranes being connected to or embedded in a support layer or the membranes being connected together to form a stable unsupported film comprising removing the cell contents from intact cells of microorganisms or breaking the intact cells and separating the membranes or membrane containing cell envelope fragments, suspending the membranes or membrane containing cell envelope fragments in a liquid medium, combining the membranes or membrane containing cell envelope fragments into a layer with a crystal lattice with continuous pores free of the protein containing molecules by depositing the membranes or membrane containing cell envelope fragments onto a support layer or introducing said fragments into a support layer or connecting said fragments together to form a stable unsupported film and a method for altering the effective passage width of the pores of a structure.

39 Claims, No Drawings

STRUCTURE WITH MEMBRANES HAVING CONTINUOUS PORES

The invention is concerned with a method for altering the effective passage width of the pores of a structure particularly suitable for an ultrafiltration membrane, which structure has at least one membrane with continuous pores or is formed of at least one such membrane, wherein the membrane or membranes which extend along plane, curved, cylindrical or vesicular surfaces, are in each case constituted of at least one layer of contiguous molecules that are joined together and in addition are arranged along a crystal lattice, namely protein molecules or protein containing molecules, with continuous pores arranged according to a lattice remaining free between the molecules in said layers, wherein these membranes are appropriately linked to or embedded in an appropriately porous carrier or are appropriately joined into an unsupported film, and wherein the protein molecules or protein containing molecules are cross-linked—through foreign molecules, if applicable—intra- and/or intermolecularly and/or to the carrier. The invention is furthermore concerned with an advantageous application of this method, a method suitable for producing such a structure, as well as advantageous applications of the structure thusly produced.

STATE OF THE ART

A structure of the aforementioned type is known from European Patent No. 2-0154620. The membranes used for the construction of this structure are constituted advantageously of protein molecules or protein containing molecules which have been obtained particularly from cell-envelopes of prokaryotic cells, by a recrystallization process called self-assembly, and thereafter deposited on and/or in a porous carrier and finally submitted to chemical cross-linking. The effective pore size at the membrane of this structure is then particularly within a diameter range of 1 to 200 nm (nanometer), but preferably within the range cf 1 to 8 nm.

In using this structure as an ultrafiltration membrane, sharp separations between molecules with small differences in molecular weight are attained, as well as higher flow rates than with previously known ultrafiltration membranes. Essentially, the desired pore diameter is obtained through the selection of the micro-organism used for producing the membrane, whose cell-envelopes have outer layers, so-called S-layers (surface layers) with pores having approximately the pore diameter aimed at. This pore diameter can be varied further by binding foreign molecules to the protein molecules or protein-containing molecules, which reach into the pore zones.

DESCRIPTION OF THE INVENTION

The invention has the initial object of indicating a method for altering the effective pore size of membranes of the aforementioned structure, which method then will permit a wider range of application of a certain structure.

In the method according to the invention for altering the effective pore size of the membranes of the aforesaid structure, the problem is solved in that through altering the medium conditions a change is effected in the conformation of the membrane molecules determining the pore form and pore size, and/or a change is effecting in the charges at the molecules within the pore zone of the membrane, and thereby a change of the effective passage width of the membrane pores. The change of the conformation and/or charge can advantageously be effected by a change of the pH-value, of the ionic strength and/or of the ion composition or the structure of the medium surrounding the structure and/or advantageously also by a change of the type of the liquid phase.

The invention is furthermore concerned with an advantageous application of this method of the invention for altering the effective passage width of the pores of a structure suitable particularly for an ultrafiltration membrane, characterized in that it is used to include in this structure substances of value, such as enzymes, active pharmaceutical substances, pesticides or similar, and/or remove these value substances from this structure.

According to an advantageous development of this application of the invention, a structure is used that forms an envelope enclosing the value substances, the surface of which envelope is in part occupied by membranes of this structure and in part is provided with an impermeable layer.

According to another advantageous development of the application of the invention, a structure is used that has membranes in vesicular form.

A last advantageous development of this application according to the invention is characterized in that for introducing the value substances into the structure, the pores of the vesicular membranes are expanded through a change in the medium, the value substances are then introduced through the expanded pores into the inside of the vesicles, and the pores then again being shrunk by way of a further change in the medium.

The invention is furthermore concerned with a method for producing a structure with membranes having continuous pores, wherein protein molecules or protein-containing molecules or fragments of layers of such molecules which in these layers are contiguously joined together and thereby arranged along a crystal lattice, wherein in these layers pores arranged according to a lattice remain free, are brought into a solution or suspension, whereupon through change of the medium conditions in the solution or suspension such conditions are created, in which these protein molecules or protein-containing molecules and/or the layer fragments combine into membranes through self-assembly. Such a method is known from European Patent No. 2-0154620. This method according to the invention is intended to solve the problem of enclosing value substances in the structure already during the production of the structure, which substances could be released in a controlled manner through enlarging the pore size in the structure.

This method of the invention is characterized in that the solution or suspension of protein molecules or protein-containing molecules or fragments of layers of such molecules is brought in contact with a value substance, in that the self-organization of the protein molecules or protein-containing molecules takes place along the surface of the value substance and in that—appropriately through treatment with mono- and/or bifunctional foreign molecules—the molecules of this membrane are substituted at reactive groups, and/or are covalently cross-linked through these reactive groups intramolecularly and/or with each other. A value substance can advantageously be used, which is bonded to or included in a carrier substance or in a carrier body, respectively.

The invention is additionally concerned with a method for producing a structure with membranes having continuous pores of the type described in European Patent No. 2-0154620, wherein the method according to the invention is to be less costly than the said described method.

This method is characterized in that cells of micro-organisms, especially cells of prokaryotic organisms, which have at least one cell-wall layer, in which protein molecules or protein-containing molecules are linked contiguous to each other and are thereby arranged along a crystal lattice, with pores arranged according to a lattice remaining free between the molecules in this cell-wall layer being broken up, if appropriate, and the cell-envelopes being subdivided into fragments, in that—after removal of the cell contents as well as of other cell-wall components or membrane lipid layers, of appropriate—the remaining cell-envelope layers or cell-wall fragments, which are constituted of the layer(s) consisting of protein molecules or protein-containing molecules and, if applicable, of the cell-wall layers adjoining them, are appropriately introduced into or deposited on a carrier, respectively, and in that—appropriately through treatment with mono- and/or bifunctional foreign molecules—the molecules of these remaining cell-envelope layers or cell-wall fragments are substituted at reactive groups and/or are appropriately covalently cross-linked through these groups intramolecularly and/or with each other and/or with the carrier. Advantagelusly, it is possible to start out with cell-envelopes of micro-organisms, which have as cell-wall layers two layers built up of protein molecules or protein-containing molecules and between them have layers appropriately consisting of peptidoglycan, pseudomureine or cellulose, with said cell-wall layers being introduced into or deposited on the carrier, respectively, in the form of cell-wall fragments.

According to an advantageous embodiment of the method of the invention, one starts out with cell-envelopes of micro-organisms, in which the protein-containing molecules forming the layers are glycoproteins.

According to another advantageous development of the invention, the micro-organism cells are broken up osmotically and/or mechanically, appropriately by means of a cell-mill or ultasonics and/or through pressure release and/or chemically, if appropriate with a French press or enzymatically, respectively.

In additional advantageous developments of the method according to the invention, there can be used as carrier, a porous layer, if appropriate a microfilter, and/or
an auxiliary layer which appropriately removed before use of the membrane, or
bodies of ionotropic gels, which are enclosed on all sides by the cell-wall fragments to be applied.

According to still other advantageous developments of the method according to the invention, the cell-wall fragments are applied by spraying and/or depositing on the carrier, and/or
application of the cell-wall fragments to the carrier is carried out under the effect of pressure and/or suction, or
the cell-wall fragments are mechanically pressed unto the carrier.

According to a further development of the method according to the invention, when carriers composed of polymers are used, the cell-wall fragments are imbedded in the porously forming carrier material during the polymerization or solidification process of the carrier.

According to yet another advantageous development of the method according to the invention, the binding of the cell-wall fragments to the carrier is reinforced by a surface heat treatment, if appropriate.

According to a further advantageous development of the invention, the method according to the invention is characterized in that the treatment with mono- and/or bifunctional foreign molecules is effected through application of gaseous and/or liquid cross-linking agents. The treatment with the gaseous or liquid cross-linking agents can advantageously be effected one after the other.

In another advantageous development of the method according to the invention, the carrier and/or the cell-wall fragments are treated with the cross-linking agents before said fragments are applied to the carrier, with the cross-linking agents being activated only after the cell-wall fragments are applied to the carrier.

According to still another advantageous development of the method according to the invention, reactive groups of the carrier and/or of the molecules of the cell-wall fragments, intended for covalent cross-linking and/or covalent linkage bond, are exposed and/or introduced prior to the application of the cell-wall fragments to the carrier.

According to an additional advantageous development of the method of the invention, the covalent cross-linking of the cell-wall fragments takes place cuncurrently with the covalent cross-linking of the protein molecules or protein-containing molecules of the applied cell-wall fragments.

In another advantageous development of the method of the invention, the cell-wall fragments applied to the carrier are covered—prior to the application of the cross-linking agent or agents, respectively—by a porous protective layer which appropriately is removed after completion of the cross-linking operation.

According to a last advantageous development of the method according to the invention, the cell-envelopes are not borken up, but rather, the components of the cells not required for the construction of the structure, such as cytoplasm membrane, cytoplasm or similar, are extracted through the pores in the cell-envelopes.

The invention lastly comprises the following applications of the structure produced according the above method of the invention, namely, use of the structure as ultrafilter, or as separating organ for a gas separation or as separating organ for ion exchange process;

the utilization of the structure as carrier for other semipermeable membranes, which stretch over pores of the membranes of the structure, whereat, appropriately, these other semipermeable membranes are cross-linked directly or through bifunctional foreign molecules with protein molecules or protein-containing molecules of the membranes of the structure through carboxyl groups and/or amino groups and/or sulfhydryl groups and/or hydroxyl groups. These other semipermeable membranes can advantageously be: hyperfiltration membranes, appropriately composed of surfactants- or surfactant-like lipoids, or separating organs for an ion exchange process, or separating organs for a pervaporation process, or solution diffusion membranes;

utilization as a separating material for penetration chromatography, with the produced structure consisting of nonbroken up cell-envelope layers, from which the components not required have been extracted and the remaining cell-envelope layers were subsequently cross-linked.

DESCRIPTION OF SEVERAL ADVANTAGEOUS WAYS TO CARRY OUT THE INVENTION

In the following it will initially be shown how, with the aid of a structure usable as an ultrafiltration membrane, the production of which has been described in Example 2 of European Patent No. 2-0154620 a change of the effective pore size can be achieved through altering the medium conditions.

This ultrafiltration membrane contains membranes built up of adjacent glycoprotein molecules, with each of the membrane pores being defined by six adjoining glycoprotein molecules. It is assumed that analogous to protein molecules in solution, which exist in only two states, namely completely unfolded and completely folded, and through a medium change only the number is changed of the molecules in one or the other state, respectively, the change of the passage width of the membrane pores caused by a medium change is based on a similar effect. A relatively small number of distinct states exists for the conformation of the glycoproteins in the pore zone and/or the charges bound there; the frequency of said states depends on the medium conditions, to wit, e.g., the pH-value and/or the ionic strength, respectively. This could have the effect at a certain medium condition the largest part of the pores would have the smallest possible pore size, while under another medium condition the largest part of the pores would have the largest possible pore size. For filtrations, for the result of which only pores of the largest pore size are effective, the effective number per unit area of these largest pores would then change continuously with the change in the medium conditions.

The filtration experiments described below confirm these expectations by the result. These experiments were conducted in each case in distilled water as well as in various buffer solutions, namely PBS (a phosphate buffered physiological sodium chloride solution), with Sörensen buffer (a precisely standardized phosphate buffer), with 0.9% NaCl and with 0.1 M CaCl$_2$. To obtain an equilibrium state with the respective buffer solution, the ultrafiltration membrane was first incubated in it for 2 hours. The ultrafiltration membranes pretreated in this manner were then inserted, for filtration tests, in an ultrafiltration device as described, e.g., in example 1 with the aid of FIG. 5 of the aforesaid European Patent No. 2-0154620, and—always in the same buffer solution as used for the incubation—the retention values (%R) of the filter was determined with respect to ovalbumin and bovine serum albumin (hereafter called BSA). In addition, comparison tests were run with the same substances in distilled water. All tests were carried through at a filtration membrane overpressure of $2.10^5$ Pa and a protein concentration of 0.8 mg protein per ml and an 80% volume reduction of the seed solution as well as under the same stirring conditions (300 r.p.m.). The results of these tests are summarized in the table below.

| Medium | Retention Capacity in R (%) | | | | |
| --- | --- | --- | --- | --- | --- |
| | Dist water | PBS | Sörensen buffer | 0.9% NaCl | 0.1 M CaCl$_2$ |
| pH | 5.5 | 7.2 | 6.8 | 5.5 | 5.5 |
| Ovalbumin (43 kD) | 83–87 | 25–30 | 27 | 27 | 27 |
| BSA (66 kD) | 95–97 | 52–56 | 57 | 53 | 57 |

As the table shows, the retention values for the proteins dissolved in the buffer solutions used decline in comparison with the situation with distilled water, and this to a great extent irrespective of the buffer used. It is to be noted that—as comparison of the values in the first column with those of the last two columns shows—the influence of the pH-value is here clearly considerably less than that of the ionic strength.

Similar tests, effected with an ultrafiltration membrane produced on the basis of Bacillus stearothermophilus 3c/NRs 1536 (see Example 1 of European Patent 2-0154620), showed that when distilled water was replaced by a buffer such as PBS and Sörensen buffer, considerably lesser changes of the retention capacity resulted. In these instances, they amounted to only about 7 to 10%.

The selection of the micro-organisms, whose S-layers or the membranes produced through recrystallization of the protein molecules or protein-containing molecules of these S-layers (hereinafter call P-membrane, as in European Patent No. 2-0154620) show a for the intended application optimal change of the effective pore size when a change occurred in the medium conditions, is most usefully done through examination of the properties of a larger number of micro-organisms.

In the hereinfollowing Examples 1 and 2 advantageous applications are described of the method for altering the pore size, described above in principle.

EXAMPLE 1

In this example, an ultrafiltration membrane is used, which has been produced on the basis of *Bacillus stearothermophilus* PV 72 as described in Example 2 of European Patent No. 2-0154620. The proteins carbonic-anhydrase (3-kD), ovalbumin (43 kD) and glyceraldehyde 3-phosphate dehydrogenase (140 kD) are to be separated by way of filtration processes:

These proteins are at first present dissolved in distilled water. In a first filtration step, carbohydratase is separated in a concentration operation, with the carbonic-anhydrase being passed through to the permeate, while ovalbumin almost completely and glyceraldehyde-3-phosphate dehydrogenase in its entirely remains in the retentate. The retentate is then rebuffered from distilled water to PBS. In the rebuffered solution, in which the retention capacity of the ultrafiltration membrane is reduced vis-a-vis ovalbumin from about 90% to 25%, ovalbumin is then washed out in a further diafiltration step, in which glyceraldehyde-3-phosphate dehydrogenase continues to remain in the retentate and can then be obtained from it.

EXAMPLE 2

In this example, the production is described of membrane vesicles with continuous vesicular pores, as well as the introduction of value substances into these vesicles.

One starts with cells of the micro-organism *Bacillus stearothermophilus* (strain PV 72), or with *Clostridium thermohydrosulfuricum* (strain L111-69), the S-layer of which is comprised of glycoproteins and has a hexagonal lattice structure (p6-symmetry) with a periodicity of 14 nm and a pore size in distilled water of about 4 nm. 1 g cell-wall preparations with 5 ml of a 5 M guanidine hydrochloride solution (in 50 mM TRIS-HCl buffer pH 7.2) are stirred for 2 hours at 25° C. "TRIS" stands here and hereinfollowing as abbreviation for tris(hydroxymethyl)aminomethane. In this step, glycoprotein molecules of the so-called S-layers are separated from the surface of the cell-walls. The thusly separated cell-walls are sedimented by centrifugation (1 hour at 20,000 g). The guanidine hydrochloride is then removed from the extract containing the glycoprotein molecules by dialysis against distilled water (pH 5.5) or 50 mM Tris-HCl-buffer (pH 7.2), in the course of which formation of vesicular membranes takes place through self-organization of the glycoproteins. These membrane vesicles suspended in distilled water are then treated with 2% glutaraldehyde as cross-linking agent (in 50 mM phosphate buffer, pH 7.2) at 20° C. for 2 hours. This results in an intra-or intermolecular cross-linkage, respectively, of the glycoproteins. After the cross-linking agent is washed out, the membrane vesicles are ready for loading with value substances. For this, the membrane vesicles are suspended in a solution of a value substance, e.g., a solution of 10 mg/ml of a protein with molecular weight of 65 to 70 kD in a 0.9% solution of NaCl (pH 5.5). Under these medium conditions, the value substance penetrates into the membrane vesicle through the latter's now expanded pores, until concentration balance sets in. After the vesicles are centrifuged away (e.g., 1 hour at 15,000 g) they are resuspended in distilled water (pH 5.5 ). By this calculated medium alteration from NaCl solution to distilled water, a reduction of the effective pore size in the membrane vesicles takes place in such a manner that the value substance can no longer reemerge from the pores and is thus kept in the membrane vesicles. For the release of the value substance from the membrane vesicles, the latter are returned to a medium, the ion concentration of which has about the same value as that which made possible the charging of the membrane vesicles with the value substance.

The method according to the invention for altering the effective pore size of a structure that has membranes with continuous pores can also be advantageously applied to a structure produced according to a method, in which the value substances are introduced into or applied to the structure, respectively, simultaneously with the formation of this structure. The following Example 3 illustrates an advantageous way to carry out this method.

EXAMPLE 3

For the fixation to a carrier of an enzyme protein forming the value substance, a polyacrylamide gel of Messrs. Biorad, Richmond, Calif., is used as carrier, which has free carboxyl groups at its pore surface. This carrier is first treated with dicyclohexyl carbodiimide and N-hydroxysuccinimide in an anhydrous solvent such as dioxan, whereby the carboxyl groups of the carrier are activated. The solvent together with the excess reagents is then washed out and the carrier is transferred into 0.1 M sodium phosphate buffer (pH 7.8). Thereupon, 10 mg of the enzyme protein per 1 g carrier are added and incubated for 5 hours at 20° C., during which the enzyme protein is linked covalently to the carrier through the latter's activated carboxyl group.

P-membranes are produced from a cell-wall preparation of the micro-organism clostridium thermohydrosulfuricum (strain L111-69) after the glycoprotein molecules of the S-layer of this micro-organism are removed with 5 M guanidine hydrochloride, and dialysis against distilled water. 10 mg of these P-membranes are then split up into its glycoprotein molecules by adding 10 ml 0.01M HCl. 10 ml of this protein solution are mixed with 10 g of the carrier, to which the enzyme protein is covalently linked, and the mixture is dialyzed at 37° C. against 10 mM $CaCl_2$-solution. As a result of the pH-value change thereby created, membranes form at the outer surface of the gel body through self-organization of the glycoproteins, which membranes envelop the gel body and the enzym fixed to it. The membranes so formed are then intra- or intermolecularly cross-linked, in a manner similar to that described in Example 2.

In the now following Example 4, advantageous ways are described to carry out a new method for producing structures that have membranes with continuous pores, namely structures of the type described in European Patent No. 2-154620, wherein in this new method the self-organization process of the protein molecules or of the protein-containing molecules, respectively, and of the layer fragments built up from these molecules to form larger membranes (designated P-membranes in European Patent No. 2-0154620) is avoided.

EXAMPLE 4

Intact cells of *Bacillus stearothermophilus* PV 72 with a wet weight of 10 g are suspended in 40 ml TRIS-HCl-buffer (50 mM, pH 7.2) and broken up by the effect of ultrasonics. The suspension was cooled in an ice bath to prevent autolytic processes. The cell-wall fragments of this suspension were pelleted by centrifugation at 20,000 g, and the lower part of the pellet, which still was comprised of intact cells, was resuspended and again submitted to ultrasonic treatment. The cell-wall fragments present in suspension are then sedimented by centrifugation at 20,000 g, resuspended and from them the cytoplasmic membrane (a double-layer lipid) is disintegrated with 0.5% Triton X-100 in 50 mM TRIS-HCl-buffer, pH 7.2) during 20 minutes at 20° C. ("TRITON X-100" stands here and in the following for octylphenol-polyethylene-glycolether, a mild detergent), whereupon the cell-wall fragments are washed several times. The cell-wall fragments, so cleaned, are now comprised of the S-layer built up of glycoprotein molecules and of the adjacent supporting layer of peptidoglycan. The size of these cell-wall fragments is controlled by electron microscopy and on average should be 500 nm.

With the aid of these cell-wall fragments an ultrafiltration membrane is now produced, which essentially has the same properties as the ultrafiltration membrane described in Example 2 of European Patent No. 2-0154620.

A nylon microfiltration membrane of Messrs. Pall, Cortland, N.Y., USA, type Ultipor $N_{66}$, with a mean pore diameter of 100 nm serves as carrier membrane for the ultrafiltration membrane. The carrier material has free amino and carboxyl groups in a ratio of 1:1. In order to release additional reactive amino and carboxyl groups, the microfiltration membrane to be used can be submitted to a treatment with hydrochloric acid 3.6 N) at 50° C. for 60 minutes, washed with distilled water and placed in an ultrafiltration unit—similar to the one described in Example 1 and with the aid of FIG. 5 of European Patent No. 2-0154620.

Application of the cell-wall fragments to the carrier and into the matrix of the carrier is effected by a depositing process—analogous to Examples 1 and 2 of European Patent No. 2-0154620. In order to attain an as uniform deposit of the cell-wall fragments as possible, 5 ml of the starting suspension are mixed with 50 ml distilled water and filled into the ultrafiltration unit, so that this suspension will initially form a layer above the inserted microfiltration membrane. Through introduction of nitrogen an overpressure of $2.10^5$Pa is created over the suspension, whereby the liquid phase is pressed through the microfilter and the cell-wall fragments are deposited on or introduced into the microfilter membrane, with application of a coating corresponding to a protein quantity of 30 ug/cm$^2$. Thereupon, by means of a nozzle arranged in the upper part of the ultrafiltration unit, glutardialdehyde (0.5% in 0.1 M sodium-cacodylate buffer, pH 7.0) is sprayed finely, as cross-linking agent, onto the cell-wall fragments deposited on the carrier, with the aid of compressed air with $3.10^5$Pa overpressure. Since after being sprayed onto the cell-wall fragments, the cross-linking agent is continually pressed through the cell-wall fragments and the microfilter membrane by virtue of the overprssure applied, no stronger liquid film is formed above the cell-wall fragments. An advantage of this type of application of the cross-linking agent is that in the at most very thin film of liquid no turbulence can be formed, which could move the cell-wall fragments deposited on the carrier and thereby disturb their final fixation. After a spray and cross-linking duration of 10 minutes, the thusly produced ultrafiltration membrane is washed three times with distilled water, and the rejection curve and flow rate are determined—as described in Example 1 of European Patent No. 2-0154620. It is thereby shown that the fact of the presence of the peptidoglycan support layer has no influence on the separation behavior of the ultrafiltration membrane.

According to an advantageous variant of this example, intact cells of the micro-organism Clostridium thermohydrosulfuricum (strain L111-69) are used as starting material for producing an ultrafiltration membrane. Intact cells of this micro-organism are first transferred into a 50 mM TRIC-HCl buffer (pH 7.2) and broken up in a French press (French Pressure Cell Press) of Messrs. American Instruments Corp., Silver Springs, Md. The cells suspended in the buffer solution are thereby compressed under high pressure and upon passing through a nozzle and because of the thereby occurring release of pressure, they experience a sudden expansion which results in a rupture of the cells. The cell-wall fragments obtained in this manner are freed of the substances contained in the cell through three times washing with the buffer solution, and the cytoplasmic membrane is disintegrated through treatment with 1% TRITON X-100 in distilled water at 37° C. for 30 minutes. The cell-wall fragments are then separated by means of centrifugation from the lipids and other impurities and then, in a manner analogous to that described in the first variant of this example, the cell-wall fragments are processed further.

Following below, several advantageous variants and examples are set forth for the various individual steps of the method of the invention.

For the selection and preparation of the carriers:

The use of nylon microfilter membranes, in which the hydrolytic splitting of the peptide bond of nylon is done by treatment with HCl or with N,N-dimethyl propanediamine, in order to obtain a greater number of free amino and/or carboxyl group in nylon. Examples of such nylon microfilter membranes are, e.g., the following types of Messrs. Pall, Cortland, N.Y., USA:

Pall Biodyne with free amino and carboxyl groups in a ratio of 1:1;

Pall Aminodyne with free amino groups;

Pall Carboxydyne with free carboxyl groups.

For the application of cell-wall fragments on a carrier membrane:

A suspension of cell-wall fragments in CH$_3$OH is applied by roller unto a smooth carrier, e.g., a glass plate, at a temperature of 50° C., whereat through evaporation of CH$_3$OH a thickening of the suspension occurs, until finally a moist layer maximum 200 nm thick will remain on the carrier. The carrier coated in this manner is placed in an atmosphere saturated with formaldehyde and incubated for approx. 30 minutes, in the course of which an intra- and intermolecular cross-linkage takes place. The continuous thin film created through the cross-linking of the cell-wall fragments is separated from the carrier by careful spraying of distilled water (4° C.) and can then, in a humid chamber, be transferred onto a stable carrier, with coarse pores, e.g. a microfilter.

For the mechanical fixation of the cell-wall fragments to or in the carrier:

On the active, i.e., with cell-wall fragments coated side of an ultrafiltration membrane—produced as in Example 1—an agar (2% in distilled water) in liquid form is poured at a temperature of 45° C. and in a layer 0.5-2 mm thick. By cooling down to 20° C., the agar solidifies in the form of a gel-layer. This gel layer then forms a protective layer for the ultrafiltration membrane and appropriately serves as roughing filter for larger impurities. It can again be removed and replaced at any time, e.g., after becoming worn or after contamination of the gel pores.

According to another variant for the production of an ultrafiltration membrane, intra- and intermolecularly cross-linked cell-wall fragments are suspended with a mixture of acrylamide, bisacrylamide, starter and catalyst, and the mixture is left to polymerize and to coagulate in the form of a layer at 20° C. A porous carrier is then formed, in which the cell-wall fragments are embedded, and which can serve as ultrafiltration membrane.

For binding protein molecules or protein-containing molecules of the cell-wall fragments to the carrier:

The free amino groups of a carrier membrane are activated with glutardialdehyde (5% in 0.1 M Naborate buffer, pH 8.0) as cross-linking agent. After the cell-wall fragments that are in suspension are deposited onto the carrier membrane, e.g., through the suction action of a vacuum (e.g., created with the aid of a water jet pump) of 5 to 6 10$^4$Pa at the vacuum side of the ultrafiltration unit, a linking takes place of the cell-wall fragments to the amino groups of the carrier membrane activated with glutardialdehyde. Thi covalent intra- and intermolecular cross-linking of the protein molecules or protein-containing molecules of the cell-wall fragments is carried through with the aid of 2% dimethyl suberimidate in 0.1 M triethanolamine, pH 8.7.

According to another variant, the free carboxyl groups of the carrier membrane are activated with EDC [abbreviation for 1-ethyl-3-(dimethyl aminopropyl)carbodiimide] (0.1 M, pH 4.75). After removal of the excess agent and stopping the reaction with 0.01 M Na-acetate buffer, pH 4.75, wash with distilled water. The cell-wall fragments suspended in the distilled water are deposited on the carrier membrane after hexamethyleneamine and 0.1 M EDC are added; depositing is effected by applying a vacuum of $5.10^4$Pa at the vacuum side of the ultrafiltration unit. The protein molecules and protein-containing molecules of the cell-wall fragments are cross-linked by way of the carboxyl groups activated by EDC and through hexamethyldiamine as bridging agent, and covalently bound to the carrier membrane. By such a covalent binding of the cell-wall fragments to the carrier membrane the stability of the ultrafiltration membrane is substantially increased; this prevents attrition by mechanical forces of the cell-wall fragments that are essential for ultrafiltration, such as may occur, e.g., in cross-flow operation with flow velocities of up to several m.s$^{-1}$.

For cross-linkage:

When using cross-linking agents in liquid phase, the cross-linking agent must be pressed through the pores of the cell-wall fragments to perform the cross-linking process, whereat the risk obtains that the flow created may move the cell-wall fragments deposited on or introduced into the carrier, which renders their final fixation on the carrier more difficult. To avoid this, cross-linking or preliminary cross-linking can also advantageously be provided by a gaseous cross-linking agent.

To this end, a nylon microfiltration membrane with a pore size of 100 nm is used as carrier and is inserted in an ultrafiltration unit. The cell-wall fragments are deposited on or introduced into the carrier membrane by applying a vacuum of $5.10^4$Pa to the vacuum side of the ultrafiltration unit. In the ultrafiltration unit, a container with formaldehyde is arranged above the carrier membrane. For the cross-linking process, the pressure chamber of the ultrafiltration unit together with the formaldehyde is heated to 80° C. The then evaporating formaldehyde, which at this temperature is present also in oligomeric form besides its monomer form, now comes in contact with the cell-wall fragments deposited on the carrier membrane, whereby—particularly through the oligomeric forms of formaldehyde, which because of their larger chain lengths extend over wider parts of the surfaces of the cell-wall fragments—an intra- or intermolecular cross-linking of the protein molecules or protein-containing molecules of the cell-wall fragments takes place, as well as their binding to the carrier membrane. Use of a gaseous or vaporous cross-linking agent has the advantage that no turbulence will be triggered, which cause the deposited cell-wall fragments to move and thus disturb their final fixation on the carrier membrane. After a cross-linking time of 2 hours, the remaining formaldehyde is washed out with distilled water for a period of 1 hour.

According to an advantageous variant of this step of the method, after such cross-linkage with the aid of a gaseous or vaporous cross-linking agentm a further cross-linking can additionally take place with liquid cross-linking agents. For this, these liquid cross-linking agents are advantageously applied by dropping onto the pre-cross-linked cell-wall fragments, and removed by suction through their pores or through the porous carrier membrane by means of a vacuum created at the back side of the carrier membrane. This will not cause any mechanical impairment of the cell-wall fragments. Liquid cross-linking agents, which can advantageously be used after a preliminary cross-linking with formaldehyde, are, e.g., dimethyl suberimidate (attack of the —NH$_2$—groups in the protein) or EDC (for cross-linking by way of —COOH—groups in the protein).

In the following Example 5, a structure is described that has vesicular membranes produced from cell-envelopes of micro-organisms, without causing a breaking up of the cell-envelopes.

EXAMPLE 5

Intact cells of the micro-organism Bacillus stearothermophilus NRS 1536 (10 g wet weight) are suspended in 50 ml 1% TRITON X-100 in 50 mM TRIS-HCl buffer (pH 7.2) and the suspension is agitated for 30 minutes at 37° C. TRITON X-100, a mild, non-ionic detergent, as a result of concentration equalization penetrates through the pores of the S-layer and the subjacent support layer of peptidoglycan belonging to the cell into the cell and there destroys the cytoplasm membrane adjoining the peptidoglycan layer. Since the cytoplasmic membrane constitutes the principal diffusion barrier of the cell-envelope, the substances contained in the cell can diffuse outside after its destruction. After the treatment with TRITON X-100, the cells are centrifuged at 20,000 g, subjected to a further extraction with TRITON X-100 for 10 minutes at 60° C. to destroy still present cytoplasmic membrane remnants, and then again centrifuged at 20,000 g. The cell-envelopes, thusly prepared, are then subjected to four successive washing steps, each consisting of agitating the cell-envelopes in distilled water for 10 minutes followed by centrifugation at 20,000 g. For the degradation of still present cell contents, such as ribosomes and nucleic acid, 2 mg ribonuclease and 2 mg desoxyribonuclease are added to a suspension of the washed cell-envelopes in 40 ml distilled water and incubated under agitation at 30° C. for 20 minutes. The suspension is then centrifuged at 20,000 g and the cell-envelopes are subjected to several steps of washing with distilled water.

The so obtained cell-wall membranes are centrifuged at 20,000 g and then again suspended in 0.1 M triethanolamine (pH 8.5), whereupon—under agitation—100 mg of a cross-linking agent, e.g., dimethyl suberimidate, are added to 10 ml of this suspension. After a reaction of 60 minutes at 20° C. the cross-linked cell then washed with distilled water and can be charged with enzyme proteins as value substances, in a manner similar to that described in Example 2.

ADVANTAGEOUS APPLICATIONS OF THE METHODS OF THE INVENTION AND OF THE STRUCTURES PRODUCED BY A METHOD OF THE INVENTION, WHICH ARE OF COMMERCIAL IMPORTANCE

Several advantageous applications of the methods of the invention and of the structures produced by the methods of the invention have been mentioned in the above described examples. These structures, especially those, the production of which is explained with the aid of Example 4 and its variants and by Example 5, can advantageously be used in ways already described in detail in European Patent No. 2-0154620.

We claim:

1. A method for producing a structure comprising at least one membrane with continuous pores having a diameter range of 1 to 8 nm extending along plane, curved, cylindrical or vesicular surfaces consisting essentially of at least one layer of contiguous identical protein containing molecules which molecules are arranged to form a crystal lattice defining continuous pores free of said molecules, the membranes being connected to or embedded in a support layer or the membranes being connected together to form a stable unsupported film comprising removing the cell contents from intact cells of microorganisms or breaking the intact cells and separating the membranes or membrane containing cell envelope fragments, suspending the membranes or membrane containing cell envelope fragments in a liquid medium, combining the membranes or membrane containing cell envelope fragments into a layer with a crystal lattice with continuous pores free of the protein containing molecules by depositing the membranes or membrane containing cell envelope fragments onto a support layer or introducing said fragments into a support layer or connecting said fragments together to form a stable unsupported film.

2. Method according to claim 1, wherein the alteration is obtained by changing the pH-value of the medium surrounding the structure.

3. Method according to claim 1, wherein alteration is obtained by changing the ion concentration and/or ionic strength of the medium surrounding the structure.

4. Method according to claim 1, wherein the alteration is obtained through changing the temperature of the medium surrounding the structure.

5. Method according to claim 1, wherein the alteration is obtained through a change of the type of the liquid phase.

6. Use of a method according to one of claims 1 and 2 through 5 for altering the effective passage width of the pores of a structure, wherein it is used to enclose value substances selected from the group consisting of enzymes, pharmaceutical active substances and pesticides within the structure and/or to remove these value substances from this structure.

7. Application according to claim 6, wherein a structure is used that forms an envelope enclosing the value substance, the surface of which is in part occupied by membranes of the structure and in part is provided with an impermeable layer.

8. Application according to claim 6, wherein a structure is used that has membranes in vesicular form.

9. Application according to claim 8, wherein for introducing the value substances into the structure, the pores of the vesicular membranes are expanded through a change in the medium, and wherein the value substances are then introduced through the expanded pores into the inside of the vesicle, and these pores are then again shrunk by way of a further change in the medium.

10. Method according to claim 1, characterized in that the micro-organisms are broken up by at least one method of the group consisting of osmotically and mechanically, appropriately by means of a cell-wall or ultrasonics, or through pressure release or appropriately with a French press or chemically or enzymatically, respectively.

11. Method according to claim 1, characterized in that at least one member of the group consisting of reactive groups of the carrier and of the molecules of the cell-wall fragments, intended for covalent cross-linking or non-covalent linkage, are exposed or introduced prior to the application of the cell-wall fragments to the carrier.

12. Method according to claim 1, characterized in that the cell-membranes are not broken up, but rather that the components of the cells that are not required for the construction of the structure, such as cytoplasmic membrane, cytoplasm or similar, are extracted through the pores in the cell-membranes.

13. Application of a structure produced according to claim 12, characterized in that it is used as separation material for penetration chromatography.

14. Application of a structure produced according to claim 1, characterized in that it is used as ultrafilter or as separating organ for a gas separation or as separating organ for an ion exchange process.

15. Application of a structure produced according to claim 1, characterized in that it is used as carrier for other semipermeable membrances which extend over at least one member of the group consisting of pores and cell-wall fragments of the structure, whereat, appropriately, these other semi-permeable membranes are cross-linked, directly or through bifunctional foreign molecules, with protein molecules or protein-containing molecules of the cell-wall fragments of the structure through at least one group selected from the group consisting of carboxyl groups and amino groups and hydroxyl groups.

16. Application according to claim 15, characterized in that these other semipermeable membranes are hyperfiltration membranes, appropriately composed of surfactants - or surfactant-like lipoids.

17. Application according to claim 15, characterized in that these other semipermeable membranes are separating organs for a gas separation.

18. Application according to claim 15, characterized in that these other semipermeable membranes are separating organs for an ion exchange process.

19. Application according to claim 15, characterized in that these other semipermeable membranes are separating organs for a pervaporation process.

20. Application according to claim 15, characterized in that these other semipermeable membranes are solution diffusion membranes.

21. Method for producing a structure with membranes having continuous pores, where protein molecules or protein-containing molecules or fragments of layers of such molecules which in these layers are contiguously joined together and thereby are arranged along a crystal lattice, where in these layers pores arranged according to a lattice remain free, are brought into a solution or suspension, whereupon through change of the medium conditions in the solution or suspension such conditions are created, in which at least one member of the group consisting of protein molecules, protein-containing molecules and the layer fragments combine into membrane through self-assembly, characterized in that this solution or suspension is brought in contact with a value substance, and in that the self-assembly of the protein molecules or protein-containing molecules takes place along the surface of the value substance and in that through treatment with at least one member selected from the group consisting of mono- and bifunctional foreign molecules—the molecules of this membrane are substituted at reactive groups, and/or are covalently cross-linked intramolecularly and/or with each other through these reactive groups.

22. Method according to claim 21, wherein a value substance is used, which is bonded to or included in a carrier substance or a carrier body.

23. A method for altering the effective passage width of the pores of a structure comprising at least one membrane with continuous pores having a diameter range of 1 to 8 nm extending along plane, curved, cylindrical or vesicular surfaces consisting essentially of at least one layer of contiguous identical protein containing molecules which molecules are arranged to form a crystal lattice defining continuous pores free of said molecules, the membranes being connected to or introduced in a support layer or the membranes being connected together to form a stable unsupported film comprising altering the effective passage width of the membrane pores by at least one method selected from the group consisting of (a) changing the pH value of the medium surrounding the membrane structure, (b) changing the ion concentration, the ion composition or the ionic strength of the medium surrounding the membrane structure, (c) by changing the temperature of the medium surrounding the membrane structure and (d) changing the type of the liquid phase surrounding the membrane structure.

24. Method according to claim 23, characterized in that one starts out with cell-envelopes of micro-organisms, which have as cell-wall layers two layers built up of protein molecules or protein-containing molecules and between them have layers appropriately consisting of peptidoglycan, pseudomureine or celluluse, and in that these cell-wall layers are deposited on or introduced into the carrier in the form of cell-wall fragments.

25. Method according to claim 23, characterized in that one starts out with cell-envelopes of micro-organisms, in which the protein-containing molecules forming the layers are glycoproteins.

26. Method according to claim 23, characterized in that a porous layer, appropriately a microfilter, is used as carrier.

27. Method according to claim 23, characterized in that an auxiliary layer, which is appropriately removed before use of the membrane, is used as carrier.

28. Method according to claim 23, characterized in that bodies of ionotropic gels are used as carriers, which are enclosed on all sides by the cell-wall fragments to be applied.

29. Method according to claim 23, characterized in that the cell-wall fragments are applied by spraying and/or depositing on the carrier.

30. Method according to claim 23, characterized in that application of the cell-wall fragments to the carrier is carried out under the effect of pressure and/or suction.

31. Method according to claim 23, characterized in that the cell-wall fragments are mechanically pressed onto the carrier.

32. Method according to claim 23, characterized in that the cell-wall fragments applied to the carrier are overlaid by an additional carrier.

33. Method according to claim 23, characterized in that when carriers composed of polymers are used, the cell-wall fragments are imbedded in the porously forming carrier material during the polymerization and/or solidification process of the carrier.

34. Method according to claim 23, characterized in that the binding of the cell-wall fragments to the carrier is reinforced by an appropriately surface heat treatment.

35. Method according to claim 23, characterized in that the treatment with mono- or bifunctional foreign molecules is effected through application of gaseous and/or liquid cross-linking agents.

36. Method according to claim 35, characterized in that the treatment with the gaseous or liquid cross-linking agents is effected chronologically one after the other.

37. Method according to claim 35, characterized in that the covalent cross-linking of the cell-wall fragments and the carrier takes place concurrently with the covalent cross-linking of the protein molecules or protein-containing molecules of the applied cell-wall fragments.

38. Method according to claim 35, characterized in that prior to the application of the cross-linking agent or agents, respectively, the cell-wall fragments applied to the carrier are covered by a porous protective layer which appropriately is removed after completion of the cross-linking operation.

39. Method according to claim 35, characterized in that the carrier and/or the cell-wall fragments are treated with the cross-linking agents before said fragments are applied to the carrier, and in that the cross-linking agents are activated only after the cell-wall fragments are applied to the carrier.

* * * * *